US011572477B2

(12) United States Patent
Cahan et al.

(10) Patent No.: US 11,572,477 B2
(45) Date of Patent: Feb. 7, 2023

(54) PREVENTION OF BIOFILM FORMATION

(71) Applicants: International Business Machines Corporation, Armonk, NY (US); Institute of Bioengineering and Nanotechnology, Singapore (SG)

(72) Inventors: Amos Cahan, Dobbs Ferry, NY (US); Hariklia Deligianni, Alpine, NJ (US); Xin Ding, Singapore (SG); Mareva B. Fevre, San Jose, CA (US); James L. Hedrick, Pleasanton, CA (US); Pei-Yun S. Hsueh, New York, NY (US); Zhen Chang Liang, Singapore (SG); Nathaniel H. Park, San Jose, CA (US); Theodore G. van Kessel, Millbrook, NY (US); Rudy J. Wojtecki, San Jose, CA (US); Yi Yan Yang, Singapore (SG)

(73) Assignees: INTERNATIONAL BUSINESS MACHINES CORPORATION, Armonk, NY (US); Institute of Bioengineering and Nanotechnology, Singapore (SG)

( * ) Notice: Subject to any disclaimer, the term of this patent is extended or adjusted under 35 U.S.C. 154(b) by 581 days.

(21) Appl. No.: 16/678,315

(22) Filed: Nov. 8, 2019

(65) Prior Publication Data
US 2020/0071543 A1   Mar. 5, 2020

Related U.S. Application Data

(62) Division of application No. 15/474,330, filed on Mar. 30, 2017, now Pat. No. 10,563,069.

(51) Int. Cl.
*A61C 8/00* (2006.01)
*C09D 5/14* (2006.01)
(Continued)

(52) U.S. Cl.
CPC ............... *C09D 5/14* (2013.01); *A01N 33/12* (2013.01); *A61B 5/6868* (2013.01);
(Continued)

(58) Field of Classification Search
CPC .. A01N 33/12; A61B 1/00142; A61B 5/6868; A61B 17/56; A61C 8/00; A61C 8/0013;
(Continued)

(56) References Cited

U.S. PATENT DOCUMENTS 4,027,392 A * 6/1977 Sawyer .................. A61C 19/00
                                                              433/32
4,027,393 A * 6/1977 Ellis ....................... A61B 90/00
                                                              604/20
(Continued)

FOREIGN PATENT DOCUMENTS

CA    2588832 A1    5/2006
CA    2629543 A1 *  5/2007  ............. A01N 33/12
(Continued)

OTHER PUBLICATIONS

Germany Office Action dated May 17, 2021, with English Translation; No. 11 2018 000 451.1, 10 pages.
(Continued)

*Primary Examiner* — Matthew M Nelson
(74) *Attorney, Agent, or Firm* — Cantor Colburn LLP; Kristofer Haggerty

(57) ABSTRACT

Antibacterial coatings and methods of making the antibacterial coatings are described herein. A first branched polyethylenimine (BPEI) layer is formed and a first glyoxal layer is formed on a surface of the BPEI layer. The first BPEI layer and the first glyoxal layer are cured to form a crosslinked BPEI coating. The first BPEI layer can be modified with superhydrophobic moieties, superhydrophilic moieties, or negatively charged moieties to increase the antifouling char-
(Continued)

acteristics of the coating. The first BPEI layer can be modified with contact-killing bactericidal moieties to increase the bactericidal characteristics of the coating.

17 Claims, 6 Drawing Sheets

(51) Int. Cl.
| | | |
|---|---|---|
| A61M 5/142 | (2006.01) | |
| C09D 7/65 | (2018.01) | |
| B05D 1/36 | (2006.01) | |
| C08G 73/02 | (2006.01) | |
| A61F 2/30 | (2006.01) | |
| B05D 5/00 | (2006.01) | |
| A01N 33/12 | (2006.01) | |
| A61B 5/00 | (2006.01) | |
| A61F 2/28 | (2006.01) | |
| A61L 27/34 | (2006.01) | |
| A61L 27/54 | (2006.01) | |
| A61L 29/08 | (2006.01) | |
| A61L 29/16 | (2006.01) | |
| A61M 5/14 | (2006.01) | |
| A61M 27/00 | (2006.01) | |
| A61N 1/378 | (2006.01) | |
| B05D 3/00 | (2006.01) | |
| C08J 3/24 | (2006.01) | |
| B05D 1/02 | (2006.01) | |
| A61F 2/07 | (2013.01) | |
| A61B 1/00 | (2006.01) | |
| A61N 1/36 | (2006.01) | |
| A61B 17/56 | (2006.01) | |
| A61M 25/00 | (2006.01) | |
| A61F 2/01 | (2006.01) | |
| A61F 2/48 | (2006.01) | |
| A61F 2/06 | (2013.01) | |
| A61F 2/14 | (2006.01) | |
| A61F 2/24 | (2006.01) | |
| A61F 2/82 | (2013.01) | |
| A61N 1/362 | (2006.01) | |
| C09D 179/02 | (2006.01) | |

(52) U.S. Cl.
CPC .......... *A61C 8/0013* (2013.01); *A61C 8/0015* (2013.01); *A61F 2/28* (2013.01); *A61F 2/30767* (2013.01); *A61L 27/34* (2013.01); *A61L 27/54* (2013.01); *A61L 29/085* (2013.01); *A61L 29/16* (2013.01); *A61M 5/14* (2013.01); *A61M 5/14276* (2013.01); *A61M 27/002* (2013.01); *A61N 1/378* (2013.01); *B05D 1/36* (2013.01); *B05D 3/007* (2013.01); *B05D 5/00* (2013.01); *C08G 73/0206* (2013.01); *C08J 3/24* (2013.01); *C09D 7/65* (2018.01); *A61B 1/00142* (2013.01); *A61B 17/56* (2013.01); *A61C 8/00* (2013.01); *A61F 2/01* (2013.01); *A61F 2/06* (2013.01); *A61F 2/07* (2013.01); *A61F 2/14* (2013.01); *A61F 2/24* (2013.01); *A61F 2/30* (2013.01); *A61F 2/482* (2021.08); *A61F 2/82* (2013.01); *A61F 2002/3006* (2013.01); *A61F 2002/30677* (2013.01); *A61M 25/0017* (2013.01); *A61M 2025/0056* (2013.01); *A61M 2205/0205* (2013.01); *A61M 2205/0238* (2013.01); *A61M 2205/04* (2013.01); *A61N 1/362* (2013.01); *A61N 1/3605* (2013.01); *A61N 1/36038* (2017.08); *A61N 1/3787* (2013.01); *B05D 1/02* (2013.01); *B05D 2505/50* (2013.01); *B05D 2518/00* (2013.01); *C08J 2379/02* (2013.01); *C09D 179/02* (2013.01)

(58) Field of Classification Search
CPC . A61C 8/0015; A61F 2/01; A61F 2/06; A61F 2/07; A61F 2/14; A61F 2/24; A61F 2/28; A61F 2/30; A61F 2/30767; A61F 2/482; A61F 2/82; A61F 2002/3006; A61F 2002/30677; A61L 27/34; A61L 27/54; A61L 29/085; A61L 29/16; A61M 5/14; A61M 5/14276; A61M 25/0017; A61M 27/002; A61M 2205/0056; A61M 2205/0205; A61M 2205/0238; A61M 2205/04
USPC .......................................................... 433/73
See application file for complete search history.

(56) References Cited

U.S. PATENT DOCUMENTS

| | | | | |
|---|---|---|---|---|
| 4,565,740 | A * | 1/1986 | Golander | C08K 3/40 514/59 |
| 4,781,591 | A * | 11/1988 | Allen | A61C 8/00 607/51 |
| 5,213,898 | A | 5/1993 | Larm et al. | |
| 5,383,935 | A * | 1/1995 | Shirkhanzadeh | A61L 27/06 623/23.49 |
| 5,725,377 | A * | 3/1998 | Lemler | A61C 8/0007 433/201.1 |
| 5,755,788 | A * | 5/1998 | Strauss | A61L 27/54 623/920 |
| 5,759,205 | A * | 6/1998 | Valentini | A61L 33/0082 623/23.72 |
| 7,207,800 | B1 * | 4/2007 | Kwan | A61C 8/0022 433/173 |
| 7,879,092 | B2 * | 2/2011 | Kim | A61C 8/0012 433/167 |
| 8,337,792 | B2 | 12/2012 | Westlund et al. | |
| 8,895,354 | B2 | 11/2014 | Kugler et al. | |
| 9,018,172 | B2 | 4/2015 | Pentelute et al. | |
| 9,109,140 | B2 | 5/2015 | Dooley | |
| 9,381,276 | B1 * | 7/2016 | Joseph | A61L 29/041 |
| 9,399,044 | B2 | 7/2016 | Cheng et al. | |
| 10,006,936 | B2 | 6/2018 | Boday et al. | |
| 2003/0194504 | A1 * | 10/2003 | Bilyk | C08J 3/245 427/515 |
| 2007/0264509 | A1 * | 11/2007 | Lai | C08G 59/3209 428/420 |
| 2008/0221681 | A1 * | 9/2008 | Trieu | A61F 2/30767 29/592 |
| 2010/0143871 | A1 * | 6/2010 | Berger | A61B 17/8685 607/51 |
| 2011/0086172 | A1 | 4/2011 | Snow | |
| 2011/0171279 | A1 | 7/2011 | Chisholm et al. | |
| 2012/0058355 | A1 | 3/2012 | Lee et al. | |
| 2012/0064489 | A1 * | 3/2012 | Rubbert | A61C 13/0004 433/175 |
| 2012/0276501 | A1 * | 11/2012 | Terkel | A61C 8/0007 433/173 |
| 2013/0302873 | A1 | 11/2013 | Singh et al. | |
| 2014/0004170 | A1 | 1/2014 | Kronen et al. | |
| 2014/0010983 | A1 | 1/2014 | Gorodisher | |
| 2014/0011161 | A1 * | 1/2014 | Berckmans, III | C23C 30/00 433/201.1 |
| 2014/0113871 | A1 | 4/2014 | Pentelute et al. | |
| 2014/0242866 | A1 | 8/2014 | Locklin | |
| 2014/0319044 | A1 | 10/2014 | Giannellis et al. | |
| 2014/0342954 | A1 | 11/2014 | Ingber et al. | |
| 2014/0369953 | A1 | 12/2014 | Purschwitz et al. | |
| 2015/0093425 | A1 | 4/2015 | Moore | |
| 2015/0148903 | A1 | 5/2015 | Robeson et al. | |
| 2015/0249137 | A1 | 9/2015 | Katsuhara et al. | |
| 2015/0328378 | A1 | 11/2015 | Schaer et al. | |

(56) References Cited

U.S. PATENT DOCUMENTS

| | | | | |
|---|---|---|---|---|
| 2015/0359613 | A1* | 12/2015 | Brodbeck | A61K 6/802 |
| | | | | 433/173 |
| 2015/0369771 | A1 | 12/2015 | Richardson-Burns et al. | |
| 2016/0002103 | A1 | 1/2016 | Wang et al. | |
| 2016/0095876 | A1* | 4/2016 | Salamone | A01N 25/34 |
| | | | | 424/59 |
| 2016/0165926 | A1 | 6/2016 | Medoff | |
| 2016/0200967 | A1 | 7/2016 | Mahoney et al. | |
| 2016/0228574 | A1 | 8/2016 | Farokhzad et al. | |
| 2016/0237305 | A1 | 8/2016 | Advincula et al. | |
| 2018/0282556 | A1* | 10/2018 | Cahan | A01N 33/12 |
| 2018/0303979 | A1 | 10/2018 | Cahan et al. | |
| 2019/0048208 | A1 | 2/2019 | Cahan et al. | |
| 2019/0048226 | A1 | 2/2019 | Cahan et al. | |
| 2019/0168172 | A1* | 6/2019 | Wang | B01D 67/0004 |

FOREIGN PATENT DOCUMENTS

| | | | | |
|---|---|---|---|---|
| CA | 2640592 | A1 * | 7/2007 | A61F 2/91 |
| CA | 2837726 | A1 * | 12/2012 | A61L 29/02 |
| CN | 1411486 | A | 4/2003 | |
| CN | 107109107 | A * | 8/2017 | A61L 29/085 |
| EP | 0346058 | A1 | 12/1989 | |
| EP | 2289971 | A1 | 3/2011 | |
| EP | 2350116 | A1 | 8/2011 | |
| JP | 62039636 | A | 2/1987 | |
| JP | H0509255 | A | 1/1993 | |
| JP | H0751353 | A | 2/1995 | |
| JP | H11255842 | A | 9/1999 | |
| JP | 4119507 | B2 * | 7/2008 | A61L 9/00 |
| JP | 2013505973 | A | 2/2013 | |
| WO | 2008106194 | A1 | 9/2008 | |
| WO | 2010038040 | A1 | 4/2010 | |
| WO | 2012077691 | A1 | 6/2012 | |
| WO | WO-2013191088 | A1 * | 12/2013 | C07D 251/24 |
| WO | 2014120095 | A1 | 8/2014 | |
| WO | 2014152423 | A1 | 9/2014 | |

OTHER PUBLICATIONS

A. J. Domb, I. Yudovin-Farber, J. Golenser, N. Beyth, E. I. Weiss, QuaternaryAmmonium Polyethyleneimine: Antibacterial Activity. J. Nanomater. 2010, 2010, DOI 10.1155/2010/826343, 13 pages.

Amos Cahan, et al.; "Prevention of Biofilm Formation"; U.S. Appl. No. 16/678,076, filed Nov. 8, 2019.

Banerjee et al., "Antifouling Coatings: Recent Developments in the Design of Surfaces That Prevent Fouling by Proteins, Bacteria, and Marine Organisms", Advanced Materials, 23(6), 2011, pp. 690-718.

Behlau, I., Mukherjee, K., Todani, A. et al. (2011). Biocompatibility and biofilm inhibition of N, N-hexyl, methyl-polyethylenimine bonded to Boston Keratoprosthesis materials. Biomaterials, 32(34), 32 pages.

Blanchemain et al., "Vascular prostheses with controlled release of antibiotics: Part 1: Surface modification with cyclodextrins of PET prostheses", Biomolecular Engineering, 24(1), 2007, pp. 149-153.

C. Tedjo, "Bacteria-surface interaction in the presence of proteins and surface attached poly(ethylene glycol) methacrylate chains", Journal of Biomedical Materials Research Part A, 82(2), 2007.

Cheng et al., "Broad-Spectrum Antimicrobial/Antifouling Soft Material Coatings Using Poly(ethylenimine) as a Tailorable Scaffold", Biomacromolecules, 16(7), 2015, pp. 1967-1977.

Davies, D., "Understanding biofilm resistance to antibacterial agents", Nature Reviews Drug discovery, 2(2), 2003, pp. 114-122.

De Prijck, K., De Smet, N., Coenye, T. et al. (2010). Prevention of Candida albicans biofilm formation by covalently bound dimethylaminoethylmethacrylate and polyethylenimine. Mycopathologia, 170(4), 213-221.

Dong et al., "SuFEx-Based Synthesis of Polysulfates", Angewandte Chemie International Edition, 53 (36), 2014, pp. 9466-9470.

Eckhardt et al., "Nanobio Silver: Its Interactions with Peptides and Bacteria, and Its Uses in Medicine", Chemical Reviews, 113(7), 2013, pp. 4708-4754.

Faris, A. H., Rahim, A. A., Ibrahim, M. N. M. et al. (2016). Combination of lignin polyol-tannin adhesives and polyethylenimine for the preparation of green water-resistant adhesives. Journal of Applied Polymer Science, 133(20), 6 pages.

Garcia et al., "Meisenheimer Complex Inspired Catalyst- and Solvent-Free Synthesis of Noncyclic Poly(aryl ether sulfone)s", Macromolecules, 47(23), 2014, pp. 8131-8136.

George, S. (2015). Nanomaterial Properties: Implications for Safe Medical Applications of Nanotechnology. Nanotechnology in Endodontics, 45-69.

Hall-Stoodley et al., "Bacterial biofilms: from the natural environment to infectious diseases", Nature Reviews Microbiology, 2(2), Feb. 2004, pp. 95-108.

Han et al., "Synthesis of fluorinated monomer and formation of hydrophobic surface therefrom," RSC Adv., 5, 2015, pp. 22847-22855.

Hasan et al., "Antibacterial surfaces: the quest for a new generation of biomaterials", Trends in Biotechnology, 31(5), May 2013, pp. 295-304.

He et al., "Synthesis and Characterization of Amphiphilic Monodisperse Compounds and Poly(ethylene imine)s: Influence of Their Microstructures on the Antimicrobial Properties", Biomacromolecules, 13(3), 2012, pp. 612-623.

Higashihara et al., "Recent Progress in High Refractive Index Polymers", Macromolecules, 48(7), 2015, pp. 1915-1929.

Ishikawa "Superbases for Organic Synthesis: Guanidines, Amidines, Phosphazenes and Related Organocatalysts," Wiley Publication, Mar. 2009, 340 pages.

Khalil et al., "Synergy between Polyethylenimine and Different Families of Antibiotics against a Resistant Clinical Isolate of Pseudomonas aeruginosa", Antimicrobial Agents and Chemotherapy, 52(5), May 2008, pp. 1635-1641.

Khan, S., Ul-Islam, M., Ullah, M. W. et al. (2015). Synthesis and characterization of a novel bacterial cellulose-poly (3,4-ethylenedioxythiophene)-poly (styrene sulfonate) composite for use in biomedical applications. Cellulose, 22(4), 2141-2148.

Kondoh, A., Yorimitsu, H., & Oshima, K. (2006). Nucleophilic aromatic substitution reaction of nitroarenes with alkyl- or arylthio groups in dimethyl sulfoxide by means of cesium carbonate. Tetrahedron, 62(10), 2357-2360.

Koplin et al., "Evaluation of the Antimicrobial Activity of Cationic Polyethylenimines on Dry Surfaces", Biotechnology Progress, 24(5), 2008, pp. 1160-1165.

Kumar et al., "Significance of microbial biofilms in food industry: a review", International Journal of Food Microbiology, 42(1), 1998, pp. 9-27.

Lander et al., "Extracytoplasmic Stress Responses Induced by Antimicrobial Cationic Polyethylenimines", Current Microbiology, 65(5), 2012, pp. 488-492.

List of IBM Patents or Patent Applications Treated as Related; (Appendix P), Filed Nov. 8, 2019, 2 pages.

Liu et al., "Antimicrobial and Antifouling Hydrogels Formed In Situ from Polycarbonate and Poly(ethylene glycol) via Michael Addition", Advanced Materials, 24(48), 2012, pp. 6484 6489.

M. Chamley et al., "Designed polymer structures with antifouling-antimicrobial properties", Reactive & Functional Polymers, 71(3), 2011, pp. 329-334.

M. M. Azevedo et al., "Polyethyleneimine and polyethyleneimine-based nanoparticles: novel bacterial and yeast biofilm inhibitors", Journal of Medical Microbiology, 63(9), 2014, pp. 1167-1173.

Matsumura et al., "Synthesis and Properties of Novel Aromatic Poly(thioether-ketone)s as Sulfur-Containing High-Performance Polymers", Macromolecules, 34(9), 2001, pp. 2848-2853.

McBain et al., "Microbial Characterization of Biofilms in Domestic Drains and the Establishment of Stable Biofilm Microcosms", Applied and Environmental Microbiology, 69(1), Jan. 2003, pp. 177-185.

Nakagawa et al. "Synthesis of Highly Refractive Poly(phenylene thioether) Derived from 2,4-Dichloro-6-alkylthio-1,3,5-triazines and Aromatic Dithiols", Macromolecules, 44(23), 2011, pp. 9180-9186.

Nakagawa et al., "Synthesis of highly refractive poly(phenylene thioether)s containing a binaphthyl or diphenylfluorene unit", Polymer Chemistry, 3, 2012, pp. 2531-2536.

(56) References Cited

OTHER PUBLICATIONS

Notification of Transmittal of the International Search Report and the Written Opinion of the International Searching Authority, International Application No. PCT/IB2018/052075, dated Jul. 26, 2018, 12 pgs.
O'Shea, J. P., Solovyeva, V., Guo, X. et al. (2014). Sequence-controlled copolymers of 2, 3, 4, 5-pentafluorostyrene: mechanistic insight and application to organocatalysis. Polymer Chemistry, 5(3), pp. 698-701.
Peraro, L., Siegert, T. R., & Kritzer, J. A. (2016). Chapter Fourteen—Conformational Restriction of Peptides Using Dithiol Bis-Alkylation. Methods in Enzymology, 580, pp. 303-332.
Price et al., "Controlled release of antibiotics from coated orthopedic implants", Journal of Biomedical Materials Research Part A, 30(3), 1996, pp. 281-286.
Raad, I., Hachem, R., Zermeno, A. et al. (1996). Silver iontophoretic catheter: A prototype of a long-term antiinfective vascular access device. Journal of Infectious Diseases, 173(2), pp. 495-498.
Sahiner et al., "The synthesis of desired functional groups on PEI microgel particles for biomedical and environmental applications", Applied Surface Science, 354, 2015, pp. 380-387.
Samberg et al., "Silver Nanoparticles in Biomedical Applications", Nanotoxicology: Progress toward Nanomedicine, CRC Press, 2014, pp. 405-421,.
Schachter, B., "Slimy business—the biotechnology of biofilms", Nature Biotechnology, 21(4), Apr. 2003, pp. 361-365.
Secinti, K. D., Ayten, M., Kahilogullari, G. et al. (2008). Antibacterial effects of electrically activated vertebral implants. Journal of Clinical Neuroscience, 15(4), pp. 434-439.
Seesukphronrarak et al., "Synthesis of Fluorene-Based High Performance Polymers. I. Poly(arylene thioether)s with Excellent Solubility and High Refractive Index", Journal of Polymer Science Part A: Polymer Chemistry, 45(14), 2007, pp. 3073-3082.
Shapiro, J. A., "Thinking about bacterial populations as multicellular organisms", Annual Reviews in Microbiology, 52(1), 1998, pp. 81-104.
Stoodley, P., & Lappin-Scott, H. M. (1997). Influence of electric fields and pH on biofilm structure as related to the bioelectric effect Antimicrobial agents and chemotherapy, 41(9), 1876-1879.
Voo et al., "Antimicrobial coatings against biofilm formation: the unexpected balance between antifouling and bactericidal behavior", Polymer Chemistry, 7(3), 2016, pp. 656-668.
Wiegand et al., "Poly(ethyleneimines) in dermal applications: Biocompatibility and antimicrobial effects", International Journal of Pharmaceutics, 456(1), 2013, pp. 165-174.
Yatvin et al., "Durable defense: robust and varied attachment of non-leaching poly"-onium" bactericidal coatings to reactive and inert surfaces", Chemical Communications, 50(67), 2014, pp. 9433-9442.
Japanese Patent Application No. 2020-503378 Notice of Reasons of Refusal dated Sep. 9, 2021, 6 pages, English Translation.
Zapp et al., "Liquid crystal and gold nanoparticles applied to electrochemical immunosensor for cardiac biomarker", Biosensors and Bioelectronics 59 (2014) 127-133.
China Rejection Decision dated Oct. 22, 2021; Application No. 201880021807.X; 4 pages.
Germany Office Action dated Jun. 23, 2021, with English Translation; Application No. 11 2018 000 451.1, 5 pages.
Japanese Notice of Reasons for Refusal dated Jun. 1, 2022, Application No. 2020-503378, 3 pages.

\* cited by examiner

PREVENTION OF BIOFILM FORMATION

DOMESTIC PRIORITY

This application is a divisional of U.S. patent application Ser. No. 15/474,330, filed Mar. 30, 2017, the disclosure of which is incorporated by reference herein in its entirety.

BACKGROUND

The present invention relates generally to antibacterial coatings for preventing and treating bacterial and microorganism colonization, biofilm formation, and infection involving an implantable medical device. More specifically, the present invention relates to systems and methods for forming chemically modified and crosslinked branched polyethylenimine (BPEI) coatings. The present invention also relates to systems and methods for forming negatively charged polymer coatings. The present invention also relates to systems and methods for negatively charging a surface of a device using an electrode.

The accumulation of microorganisms on wetted surfaces, or biofouling, is a ubiquitous problem for materials in a broad range of applications such as medical devices, marine instruments, food processing, and even domestic drains. Generally, bacteria initiate biofouling via the formation of biofilms, which are formed of highly ordered adherent colonies, most frequently within a self-produced matrix of extracellular polymeric substance.

The use of implantable devices (such as prosthetic joints, heart valves, artificial hearts, vascular stents and grafts, cardiac pacemakers and defibrillators, nerve stimulation devices, gastric pacers, vascular catheters and ports (e.g., Port-A-Cath)) is growing, and so is the number of immunocompromised patients, as a result of advanced therapeutics. Infection is a problem for implanted medical devices. The surfaces of implanted materials and devices represent immunocompromised local areas in which bacterial colonization and subsequent biofilm formation is difficult to diagnose and treat. Biofilms are the main culprit for persistent infections, owing to their treatment resistance, the potential release of harmful toxins, and the ease with which the microorganisms spread, which can lead to malfunction of implantable devices on which they develop (e.g. catheter occlusion) or septic emboli seeding microorganisms in remote sites.

Extreme measures such as removal of the infected implanted device from the patient's body are often the only viable management option. Although disinfection techniques and prophylactic antibiotic treatment are used to prevent colonization during procedures, this practice is not 100% effective in preventing perioperative bacterial colonization. Moreover, the risk of bacterial colonization on a prosthetic joint is present long after its implantation. For example, with S. aureus bacteremia, the risk for colonization on a prosthetic joint approaches 25%.

Antibiotic treatments to eliminate colonization and infection associated with implantable substances and devices are limited in their ability to eradicate bacteria and fungi involved in these processes. There are multiple reasons for this, including reduced antibiotic concentration deep inside the biofilm due to limited diffusion, inability of antibiotics in general to eliminate "the last" pathogen cells (usually accomplished by the immune system, which does not function well in the setting of implantable devices), and the ability of microorganisms to persist, i.e., become metabolically inactive and thus functionally relatively resistant to antibiotics. Antibiotic resistance makes treating device-associated infections even more challenging. In fact, antibiotic resistance is frequently encountered with microorganisms that cause device-associated infections (e.g., Enterococci, Staphylococci).

Consequently, considerable efforts were dedicated in recent years to developing antibacterial surfaces. Such surfaces can be classified into two categories: (i) antifouling surfaces that prevent the adhesion of microorganisms and (ii) bactericidal surfaces that trigger bacteria killing. Typical strategies for the design of antibacterial surfaces involve either supramolecular (non-covalent) coating of the surface or modification of the surface (i.e., chemical modification or structuring). Antifouling properties can be obtained by the incorporation of $\alpha,\omega$-diamino-functionalized poly(ethylene glycol) (PEG, molar mass of 4,600 g/mol) to increase hydrophilicity to resist bacteria attachment, while bactericidal characteristics can be gained by functionalization with releasable bacteria-killing substances, such as silver nanoparticles (Ag NPs) and antibiotics, or by decoration with contact-killing bactericidal moieties like quaternary ammonium salts. Current technologies, however, suffer from poor long-term antibacterial performance and stability, the undesirable development of bacterial resistance, or limited scalability to an industrial setting.

SUMMARY

The current invention is directed to systems and methods for forming chemically modified and crosslinked branched polyethylenimine (BPEI) coatings, negatively charged polymer coatings, and negatively charged device surfaces using an electrode to prevent and treat bacterial and microorganism colonization, biofilm formation, and infection.

In some embodiments, BPEI is used as a support for attaching hydrophobic or hydrophilic moieties to improve the antimicrobial/antifouling properties of the final material. Aqueous solutions of BPEI and glyoxal are successively sprayed on substrates and afford, after curing, a crosslinked coating that provides the advantage of a versatile technology platform for the economical and large-scale application of antimicrobial materials to medical devices.

In some embodiments, the BPEI is modified with materials having a negative surface electric charge. A coating formed in this manner repels bacteria that would otherwise adhere to the surface of an implantable device. The same technology can be used to prevent colonization of medical equipment such as endoscopes, laparoscopes, endoscopes, and surfaces in the healthcare system (e.g. in the patient environment).

According to one or more embodiments of the present invention, a method for forming a crosslinked BPEI coating is provided. The method includes forming a first BPEI layer on a substrate. A first glyoxal layer is formed on a surface of the first BPEI layer. The first BPEI layer and the first glyoxal layer are cured at a temperature operable to form the crosslinked BPEI coating. The coating provides the technical benefit of a versatile technology platform for the economical and large-scale application of antifouling and bactericidal materials to the surface of implantable and non-implantable medical devices.

The first BPEI layer can be modified with superhydrophobic moieties, superhydrophilic moieties, negatively charged moieties, or a combination of the foregoing to provide the technical benefit of a coating having improved antifouling characteristics. The first BPEI layer can be modified with contact-killing bactericidal moieties to provide the technical benefit of a coating having improved bactericidal characteristics.

According to one or more embodiments of the present invention, an apparatus for preventing and treating bacterial and microorganism colonization, biofilm formation, and infection is provided. The apparatus includes an implantable medical device and a glyoxal-crosslinked BPEI coating formed on a surface of the implantable medical device. Amines of the glyoxal-crosslinked BPEI coating are covalently bonded to superhydrophobic moieties or negatively-charged moieties to provide the technical benefit of a coating having improved antifouling characteristics.

According to one or more embodiments of the present invention, a method for forming a negatively charged polymer coating is provided. The method includes providing a polymer and functionalizing the polymer with a bio-compatible moiety having a negative Zeta potential. In some embodiments, the polymer is hydroxyapatite or poly(3,4-ethylenedioxythiophene) (PEDOT) and the bio-compatible moiety is a carboxylic negative group or a polystyrene sulfonate group. In this manner, the technical benefit of a coating having a negative surface charge is provided.

According to one or more embodiments of the present invention, an apparatus for preventing and treating bacterial and microorganism colonization, biofilm formation, and infection is provided. The apparatus includes an implantable medical device and a negatively charged coating formed on a surface of the implantable medical device. The negatively charged coating provides the technical benefit of a coating having improved antimicrobial characteristics. In some embodiments, a power source is embedded within the implantable medical device for providing the technical benefit of a self-contained device for maintaining the negatively charged coating. The power source can be triggered to maintain the negatively charged coating by a change in local pH or a rise in body temperature to provide the technical benefit of an implantable medical device having an efficient power source that triggers only when necessary.

Implantable medical devices to which a coating of the present invention can be applied include, but are not limited to, a prosthetic joint, a vascular line, stent or graft, a venous filter, a tooth implant, a cochlear implant, a metal used for bone fracture internal fixation, a urinary catheter, a ventriculoperitoneal shunt, a cardiac or nerve pacemaker, a heart valve, or a ventricular assist device.

Other advantages and capabilities of the invention will become apparent from the following description taken in conjunction with the accompanying drawings showing the embodiments and aspects of the present invention.

BRIEF DESCRIPTION OF THE DRAWINGS

The subject matter of the present invention is particularly pointed out and distinctly defined in the claims at the conclusion of the specification. The foregoing and other features and advantages are apparent from the following detailed description taken in conjunction with the accompanying drawings in which:

DETAILED DESCRIPTION

Figure 1:
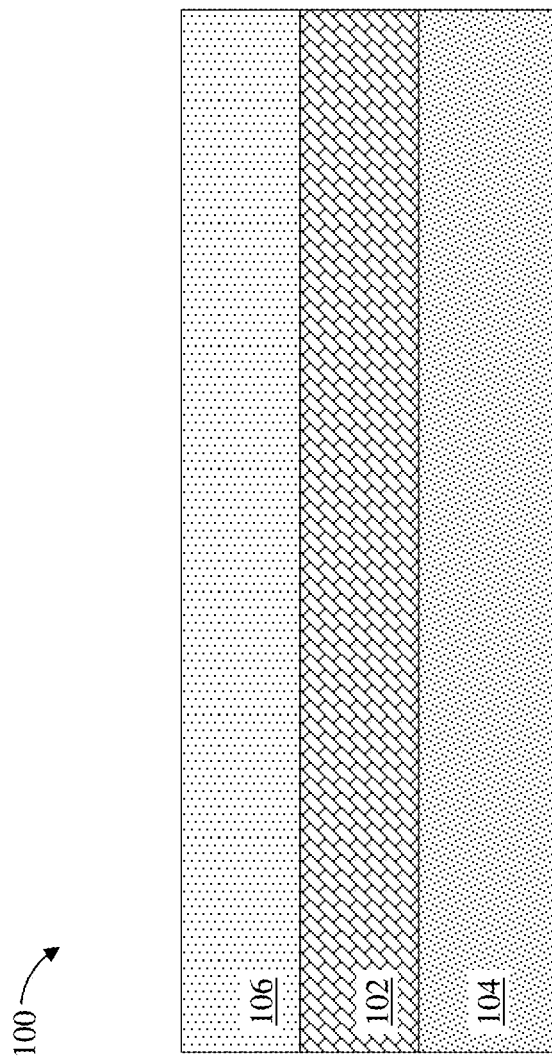
FIG. 1 depicts a cross-sectional view of a structure having a first BPEI layer formed on a substrate during an intermediate operation of a method of fabricating a BPEI coating according to one or more embodiments of the present invention.

Various embodiments of the present invention are described herein with reference to the related drawings. Alternative embodiments can be devised without departing from the scope of this invention. It is noted that various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements. The term "selective to," such as, for example, "a first element selective to a second element," means that a first element can be etched and the second element can act as an etch stop. The term "conformal" (e.g., a conformal layer) means that the thickness of the layer is substantially the same on all surfaces, or that the thickness variation is less than 15% of the nominal thickness of the layer.

As used herein, the terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

Turning now to a description of technologies that are more specifically relevant to the present invention, as previously noted herein, conventional antibacterial materials that leverage antifouling or bactericidal surfaces suffer from poor long-term antibacterial performance and stability, the undesirable development of bacterial resistance, or limited scalability to an industrial setting. Moreover, while bacterial cells' lysis on biocide-functionalized surfaces reduces the rate of biofilm formation, a combination of both antifouling and bactericidal properties is desirable to insure the long-term efficacy of the surfaces.

Amongst antimicrobial materials, polyethylenimine (PEI) represents an interesting alternative to conventional materials. PEI is commercially-available, exhibits tertiary/secondary/primary amines available for attachment of functional groups, and is thought to kill bacteria in a contact-killing fashion (i.e., no release of toxic moieties from the surface is needed). The possibility for the chemical modification of PEI to make it more hydrophobic and/or to attach permanent charges has been widely studied. PEI nanoparticles, cross-linked by reductive amination or nucleophilic substitution, are efficient antimicrobial agents. Conventional methods for incorporating PEI antimicrobial materials, however, require multistep-modification procedures, rely on harsh, environmentally unfriendly processing, and/or lack a scalable deposition method applicable to an industrial setting. Furthermore, when used as a coating, PEI suffers, like most antimicrobial materials, from poor long-term efficacy.

Therefore, there remains a clear need for an environmentally friendly method for protecting surfaces and devices for prolonged periods of time using a combined antimicrobial/antifouling strategy for preventing biofilm formation. Accordingly, it is to solving this and other needs that the present invention is directed.

Example methods for forming chemically modified and crosslinked BPEI coatings, negatively charged polymer coatings, and negatively charged device surfaces using an electrode to prevent and treat bacterial colonization, biofilm formation, or infection and the resulting structures therefrom in accordance with embodiments of the present invention are described in detail below by referring to the accompanying drawings in FIGS. 1-6.

In some embodiments, branched PEI (BPEI) is cross-linked at the surface of a substrate using its available primary amines, which are reacted with glyoxal. The reaction of the primary amines with glyoxal can lead to a mixture of products (i.e., α-hydroxy amine 1, imine 2, and 4/1 adducts 3) as depicted in Scheme 1:

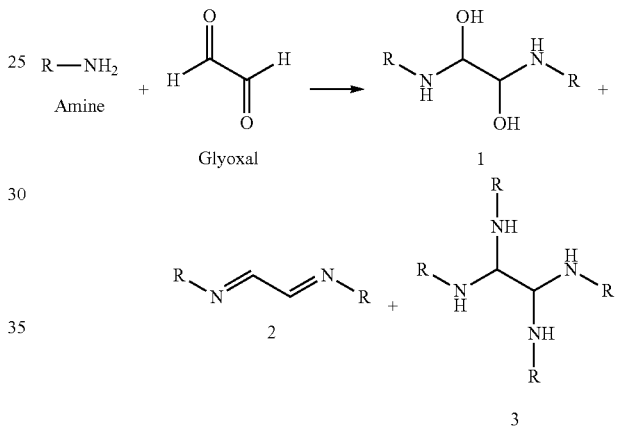

The occurrence of each product depends on the nature of the amine, stoichiometry, solvent, and temperature. In model studies performed at room temperature (RT) and analyzed by nuclear magnetic resonance spectroscopy (NMR), the major product observed is the imine 2. However, traces of other products which can be attributed to the presence of 3 were observed while varying the stoichiometry. Moreover, mixing PEG with 0.5 equiv. glyoxal in N-methyl-pyrrolidone (NMP) results in the gelation of the reaction mixture after about four (4) hours, evidencing the formation of 3, likely kinetically-quenched in the network.

In some embodiments, both BPEI and glyoxal are deposited from water. Advantageously, this approach allows for a more environment-friendly process. Most interestingly, the reaction of BPEI with glyoxal is very fast and leads to an immediate gelation of the reaction medium when mixing aqueous solutions of BPEI at a concentration of greater than about 25 weight percent and glyoxal at a concentration of greater than about 5 weight percent. Taking advantage of this fast gelation, a layer-by-layer process can be achieved.

FIG. 1 illustrates a cross-sectional view of a structure 100 having a first BPEI layer 102 formed on a substrate 104 during an intermediate operation of a method of fabricating a BPEI coating according to one or more embodiments. The BPEI layer 102 is viscous enough to allow for good coverage of the substrate surface. A first glyoxal layer 106 is formed on a surface of the first BPEI layer 102. The first BPEI layer 102 and the first glyoxal layer 106 can be formed or deposited over the substrate 104 using any suitable process, such as, for example, deposition by dip-coating or spray-coating. In some embodiments, the first BPEI layer 102 and the first glyoxal layer 106 are successively sprayed onto the substrate 104 (e.g., APTES-functionalized glass substrate) from nozzles positioned over the substrate 104 at a distance of about 15 centimeters at a pressure of about 25 psi.

Additional alternating layers of BPEI and glyoxal can formed on the structure 100 in a similar manner. The total number of deposited layers can be chosen depending on the desired thickness of the final coating. In some embodiments, the structure 100 is formed from a single layer of BPEI and glyoxal (2 total layers). In some embodiments, four (4) or nine (9) layers are used, although other thicknesses (and consequently, total number of layers) are within the contemplated scope of the invention. In some embodiments, depending on the concentration of the BPEI layers, the concentration of the glyoxal layers, and the temperature (e.g., for solutions having greater than about 25 wt % BPEI and 5 wt % glyoxal at a temperature of about 20 degrees Celsius), immediate gelation can be observed.

In some embodiments, the BPEI layers (e.g., first BPEI layer 102) and the glyoxal layers (e.g., first glyoxal layer 106) are deposited over the substrate 104 from 22 mL-reservoir spray guns. In some embodiments, a 2.5 wt % glyoxal solution in water is transferred into a 22 mL-reservoir of a first spray gun and PEI (1.8 k molar mass with 0.31 mmol or 3.19 mmol —NH2 moieties) in 6.8 g MilliQ water is transferred into a 22 mL-reservoir of a second spray gun. In some embodiments, the substrate 104 can be transferred on a hot plate for cure after the spray coating process.

Figure 2:
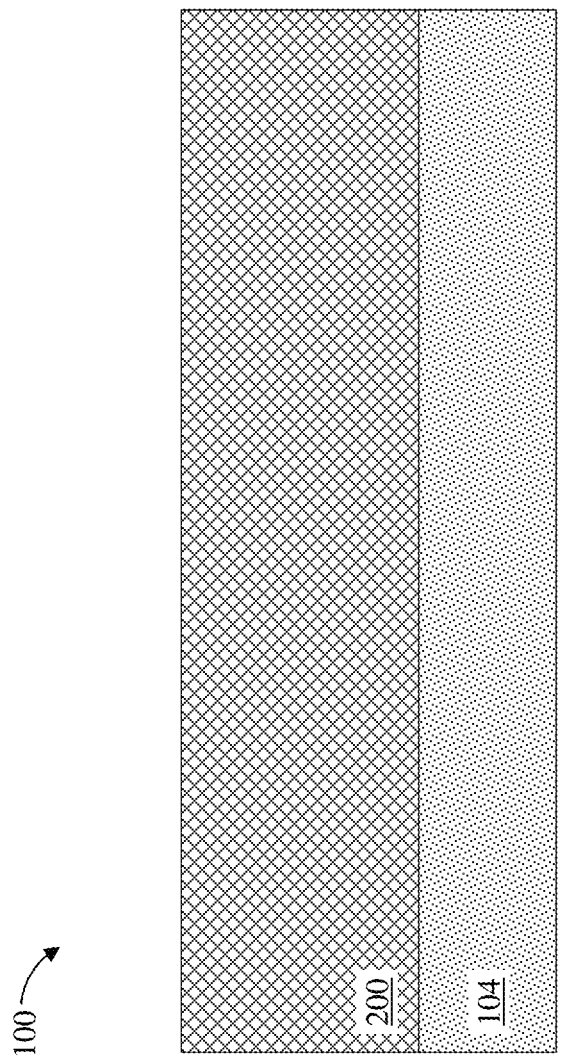
FIG. 2 depicts a cross-sectional view of the structure after curing the first BPEI layer and a first glyoxal layer to form a homogeneous and glyoxal-crosslinked coating during an intermediate operation of a method of fabricating a BPEI coating according to one or more embodiments of the present invention.

FIG. 2 illustrates a cross-sectional view of the structure 100 after curing the first BPEI layer 102 and the first glyoxal layer 106 to form a homogeneous and glyoxal-crosslinked coating 200 (hereinafter, coating 200) during an intermediate operation of a method of fabricating a BPEI coating according to one or more embodiments. In some embodiments, the first BPEI layer 102 and the first glyoxal layer 106 are cured at a temperature of about 30 degrees Celsius for about 1 hour. In some embodiments, the first BPEI layer 102 and the first glyoxal layer 106 are cured at a gradually increasing temperature of about 30 to about 120 degrees Celsius over about 1 hour. In some embodiments, the first BPEI layer 102 and the first glyoxal layer 106 are cured at a temperature of about 120 degrees Celsius for about 1 hour. In some embodiments, a three stage thermal treatment is used to cure: (1) a first stage cure at a temperature of 30 degrees Celsius for 1 hour; (2) a second stage cure at a gradually rising temperature of about 30 degrees Celsius to about 120 degrees Celsius over 1 hour; and (3) a third stage cure at a temperature of about 120 degrees Celsius for 1 hour. The substrate 104 is then allowed to cool down to room temperature. Curing the coating 200 allows for the removal of water (or any residual solvent) and ensures a maximum crosslinking density.

Figure 3:
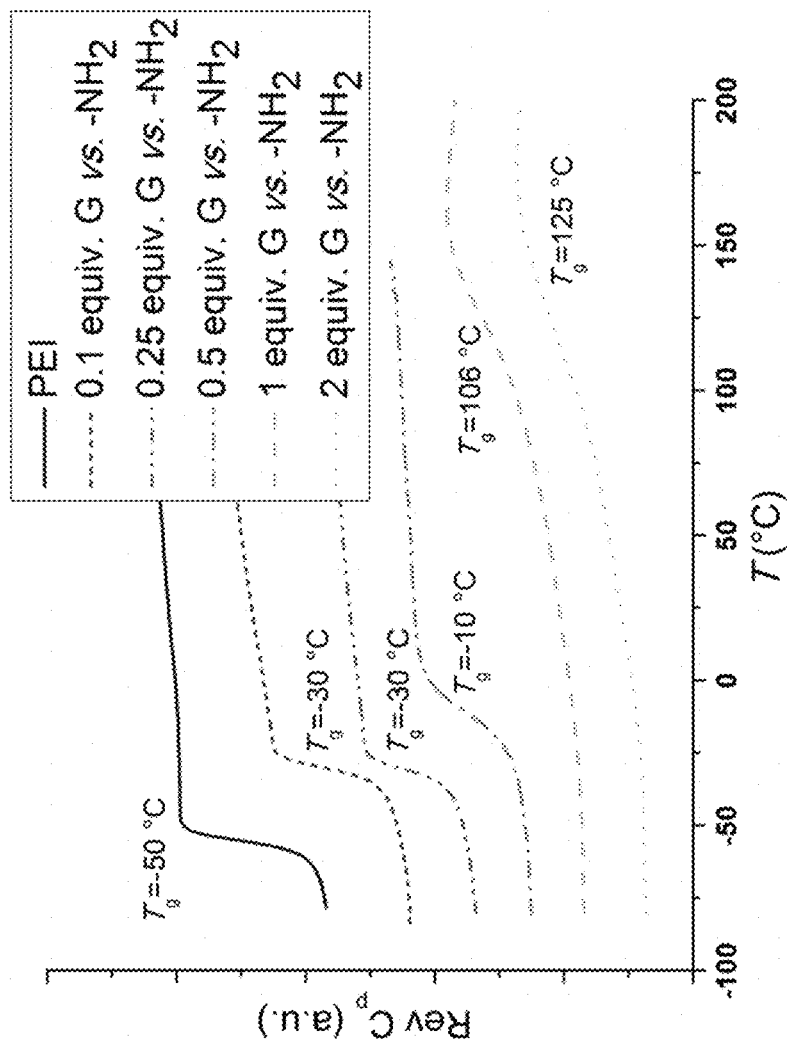
FIG. 3 depicts differential scanning calorimetry (DSC) traces of homogeneous and glyoxal-crosslinked coatings formed according to one or more embodiments of the present invention.

The crosslinking density and properties of the final coating (glass transition temperature (Tg), water resistance, etc.) can be modified by varying the amount of glyoxal vs. primary BPEI amines, as evidenced by differential scanning calorimetry (DSC) traces shown in FIG. 3. For instance, increasing the amount of glyoxal from 0.5 equiv. to 2 equiv. vs. the amount of primary amines of a BPEI exhibiting of molar mass 1,800 g/mol led to a 135 degree Celsius increase of Tg.

The coating 200 can be selectively formed or modified to increase its antifouling and bactericidal properties. Antifouling properties can be gained, for example, by covalent attachment or functionalization of the BPEI layers (e.g., the first BPEI layer 102) prior to or during curing with superhydrophobic, superhydrophilic, or negatively charged moieties. Bactericidal characteristics can be gained by functionalization of the BPEI layers (e.g., the first BPEI layer 102) with releasable bacteria-killing substances, such as silver nanoparticles (Ag NPs) and antibiotics, or by incorporating contact-killing bactericidal moieties like quaternary ammonium salts (e.g., contact-killing cationic polymers).

In some embodiments, amines of the first BPEI layer 102 are covalently bonded with moieties prior to curing. This reaction can lead to the incorporation of superhydrophobic (as depicted in Scheme 2) or negatively-charged moieties (as depicted in Scheme 3).

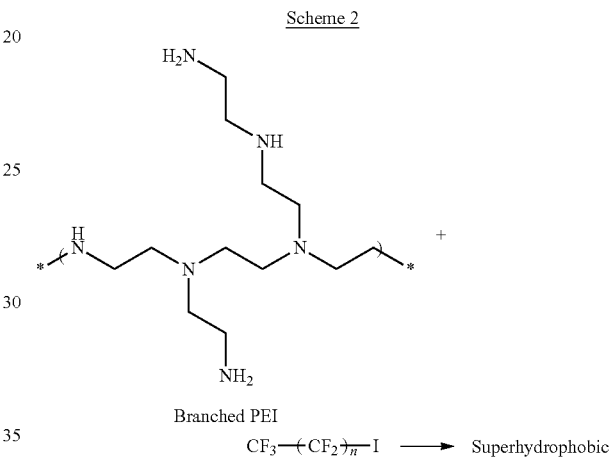

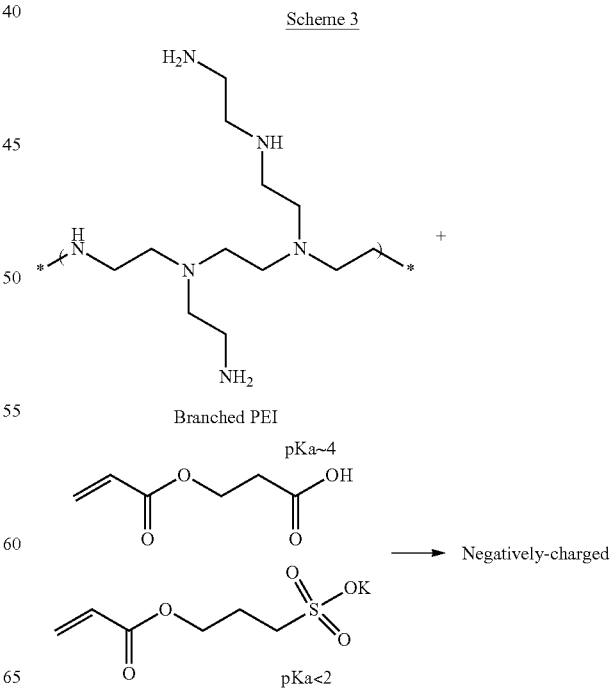

In some embodiments, hydrophobic, superhydrophilic, or negatively-charged moieties are incorporated into the coating 200 via the reaction with glyoxal as depicted in Schemes 4, 5, and 6, respectively. In Scheme 5, for example, α,ω-diamino- ($M_n$=4,600 g/mol) and α-methoxy,ω-amino- ($M_n$=2,000 g/mol) functionalized PEG are chemically incorporated into the BPEI/glyoxal mixture via the reaction with glyoxal during curing.

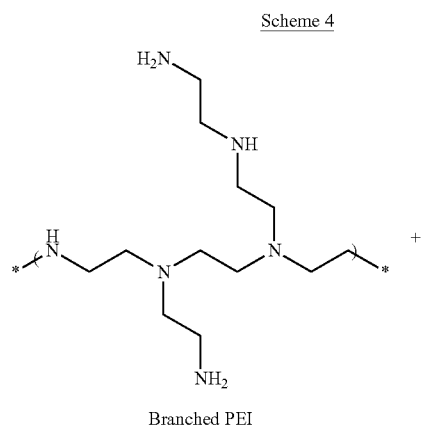

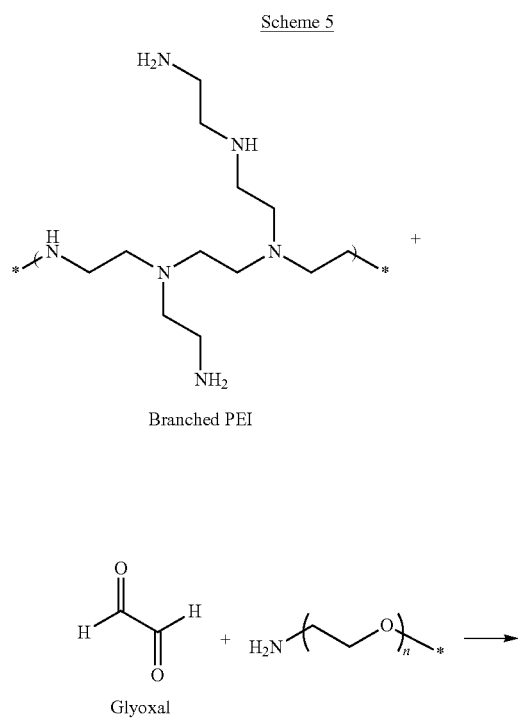

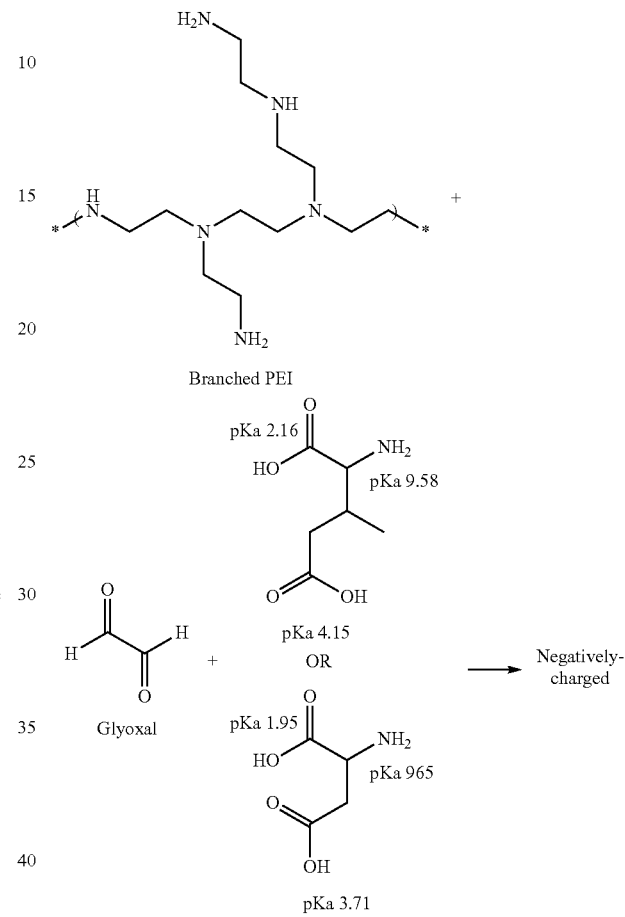

In some embodiments, the first BPEI layer 102 is functionalized with cationic polymer moieties in an aqueous solution. In this manner, the coating 200 is modified with bactericidal characteristics (i.e., the bactericidal character of the coating 200 is brought about by the amines of the first BPEI layer 102, which are partially positively charged in the aqueous solution). In some embodiments, the cationic moieties can be permanently charged by quaternization. In some embodiments, the amines of the first BPEI layer 102 are quaternized by halogenoalkanes or halogenoaryls.

In some embodiments, the adhesion of the coating 200 on the substrate 104 can be promoted either by modification of the substrate 104 or by the addition of adhesion promoter moieties. For example, in some embodiments, the surface of the substrate 104 can be functionalized with —$NH_2$ moieties via condensation of (3-aminopropyl)triethoxysilane (APTES). The amine moieties attached at the surface of the substrate react with glyoxal during the curing process. In some embodiments, catechol containing moieties are added either or both of the BPEI/glyoxal mixtures to promote the adhesion of the coating 200 to the substrate 104.

Figure 5:
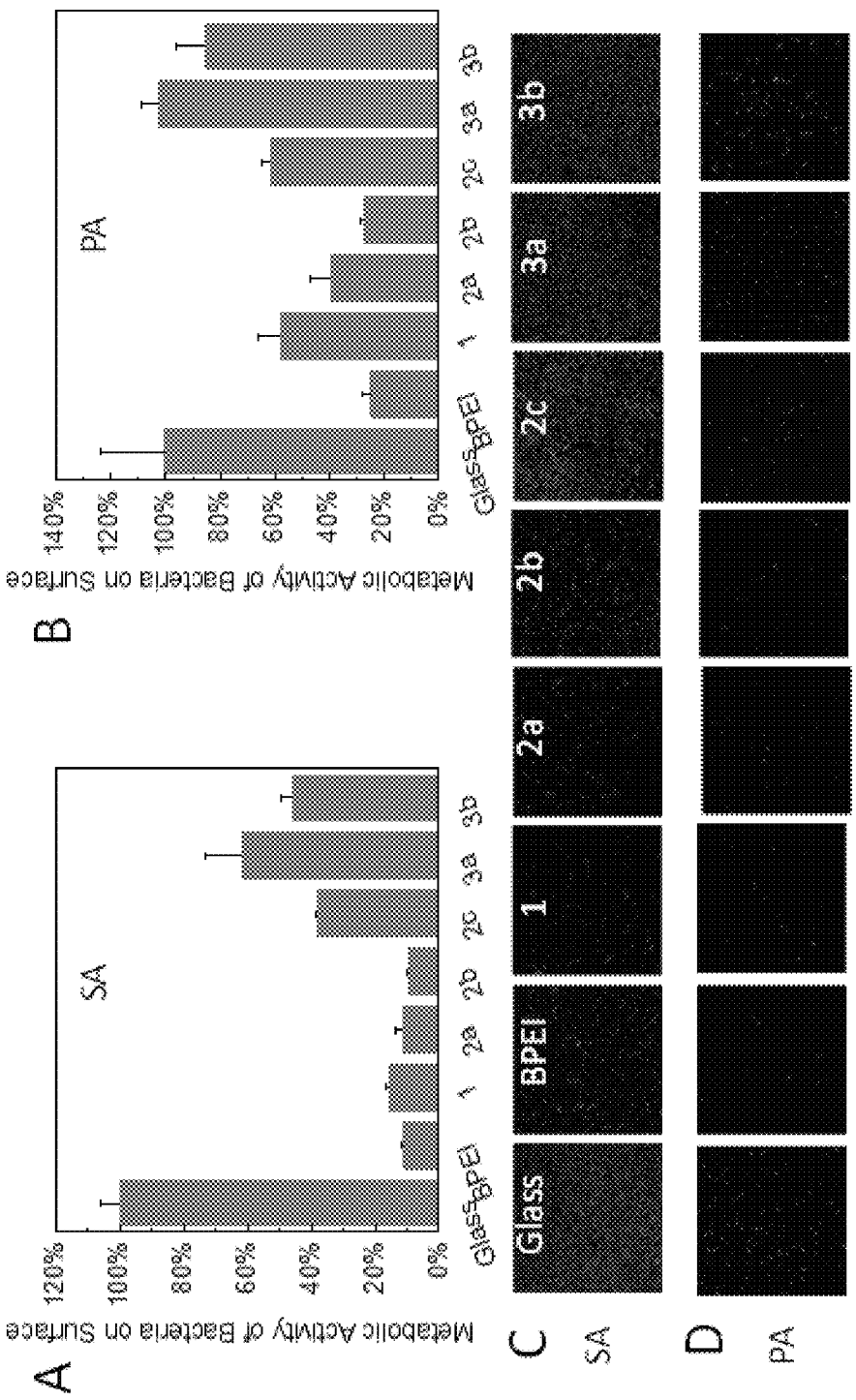
FIG. 5 depicts one (1) day incubation XTT assays (A, B) and live/dead bacteria stainings (C, D) for *S. aureus* (SA) and *P. aeruginosa* (PA) as applied to glass (control) and PEI-based coatings formed according to one or more embodiments of the present invention.

FIG. 5 depicts one (1) day incubation XTT assays (A, B) and live/dead bacteria stainings (C, D) for S. aureus (SA)

and *P. aeruginosa* (PA), respectively, as applied to glass (control) and PEI-based coatings formed according to one or more embodiments of the present invention. *S. aureus* (SA) and *P. aeruginosa* (PA) were chosen to evaluate the antimicrobial/antifouling properties of the PEI-based coatings as they are Gram-positive and Gram-negative bacteria, respectively, known to be responsible for hospital-acquired infections. Both SA and PA were able to colonize on control unmodified glass substrates. In particular, a dense layer of SA was detected on glass surfaces after incubation for only one (1) day. The glass substrates can be prepared using known techniques. For example, 3"×2" glass microscope slides can be dipped in a surfactant solution overnight. The slides can then rinsed with water and ethanol and dried. The slides can then be treated by UV/ozone for 15 min. These clean slides can then be dipped in a 10% APTES solution in ethanol for 30 minutes and thoroughly rinsed with ethanol before drying. Aluminum tape (e.g., 80 μm thickness) boundaries can be installed and the slides can be kept under nitrogen before spray coating.

Upon coating with functional PEI/glyoxal, most surfaces demonstrated some antifouling activity. For instance, the unmodified BPEI coating (BPEI) significantly reduced the fouling of both SA and PA to 11% and 25%, respectively, as compared to control glass substrates. Coating with PEG-functionalized BPEI (1, BPEI functionalized with hydrophilic $NH_2$-$PEG_{4.6\ k}$-$NH_2$ and $mPEG_{2\ k}$-$NH_2$) did not improve the antifouling activity against SA. This could be explained by the similar surface hydrophilicities of PEG/BPEI and unmodified BPEI coatings. Moreover, the 1 coating had a lower antifouling activity against PA, likely because of PEG chains shielding the cationic charges of BPEI and thus reducing the antibacterial efficacy of BPEI.

BPEI coatings formed using negatively-charged glutamic acid (2a, BPEI functionalized with $NH_2$-$PEG_{4\ k}$-$NH_2$/negatively-charged glutamic acid), aspartic acid (2b, BPEI functionalized with $NH_2$-$PEG_{4\ k}$-$NH_2$/negatively-charged aspartic acid), and carboxylate acrylate (2c, BPEI functionalized with $NH_2$-$PEG_{4\ k}$-$NH_2$/negatively-charged carboxylate acrylate) should electrostatically repel the negatively-charged bacteria. It was found, however, that the 2a and 2b coatings displayed equally good antifouling activity as unmodified BPEI coating. Although the negatively-charged moieties might repel the bacteria, the overall charge of the coating was decreased, which can result in decreasing the antibacterial effect of BPEI.

BPEI coatings fluorinated to increase hydrophobicity were found to successfully increase the surface hydrophobicity of the coatings with contact angles up to 76° (3a, BPEI functionalized with hydrophobic fluorinated moieties of $CF_3$—$CF_2$—) and 73° (3b, BPEI functionalized with hydrophobic fluorinated moieties of $CF_3$—$(CF_2)_5$—). However, SA and PA fouling increased on these coatings as compared to the unmodified BPEI surfaces, likely owing to a decrease of the cationic charges content after partial substitution of the BPEI's amines to install the fluorinated moieties.

Figure 6:
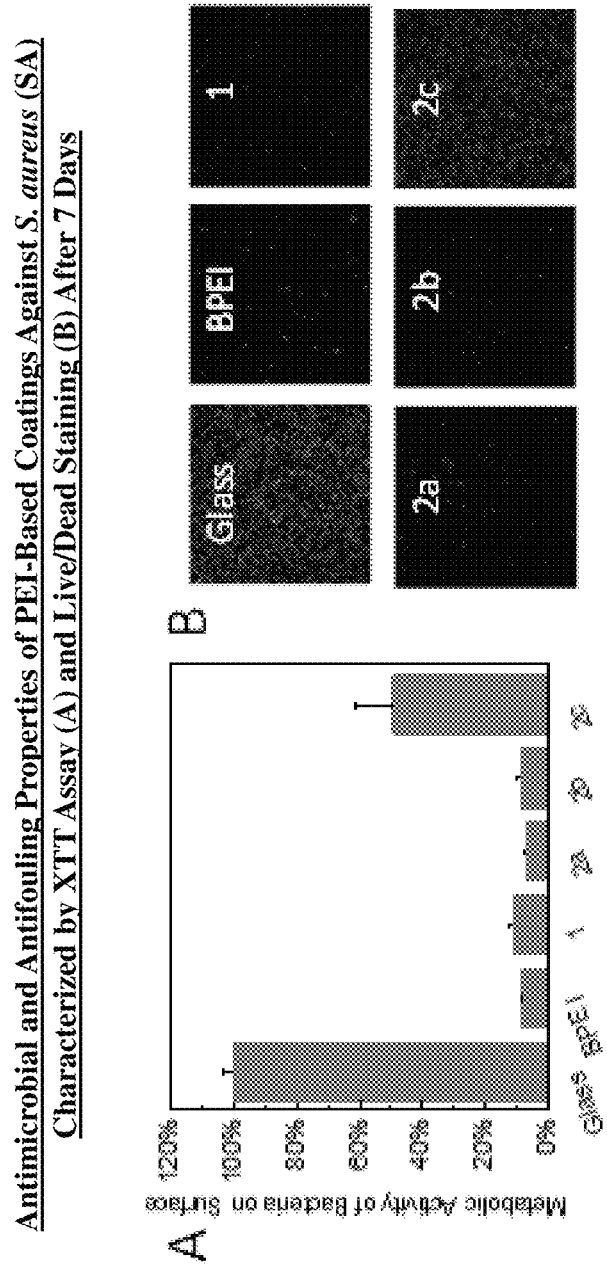
FIG. 6 depicts a seven (7) day SA incubation XTT assay (A) and live/dead bacteria staining (B) as applied to glass (control) and PEI-based coatings formed according to one or more embodiments of the present invention.

The long-term antimicrobial/antifouling activities of BPEI-based coatings which showed promising results in the 1 day incubation tests (BPEI, 1, 2a, 2b, and 2c, as depicted in FIG. 5) were incubated with SA for 7 days. FIG. 6 depicts a seven (7) day SA incubation XTT assay (A) and live/dead bacteria staining (B) as applied to glass (control) and PEI-based coatings BPEI, 1, 2a, 2b, and 2c. The growth media was replaced with fresh one daily. All BPEI-based films remained intact after incubation with SA for 7 days. The XTT and live/dead staining results evidenced that BPEI-based coatings BPEI, 1, 2a, 2b, and 2c exhibited excellent antifouling activities after 7 days, with bacteria counts comparable to these observed after 1 day incubation (as depicted in FIG. 6), regardless of the modification strategy.

Various schemes have been described for modifying the antifouling and bactericidal characteristics of the coating 200. It is understood that these schemes are merely representative of all available schemes, and that other, similar schemes can be used to modify the coating 200. Long-term stability and efficacy of antimicrobial coatings can be optimized by balancing the hydrophobicity or hydrophilicity of the coating against the electrostatic attraction or repulsion of the coating with alive/dead bacteria.

In some embodiments, negatively charged polymer coatings are formed to prevent and treat bacterial and microorganism colonization, biofilm formation, and infection involving an implantable medical device. In some embodiments, the coating 200 is made by functionalizing a commercially available polymer with bio-compatible materials having a negative Zeta potential. In some embodiments, for example, the coating 200 is hydroxyapatite functionalized with carboxylic COO– negative groups (e.g., dodecanedioic acid). In some embodiments, the coating 200 is poly(3,4-ethylenedioxythiophene) (PEDOT) functionalized with polystyrene sulfonate groups. These reactions can lead to the example coatings depicted in Scheme 7:

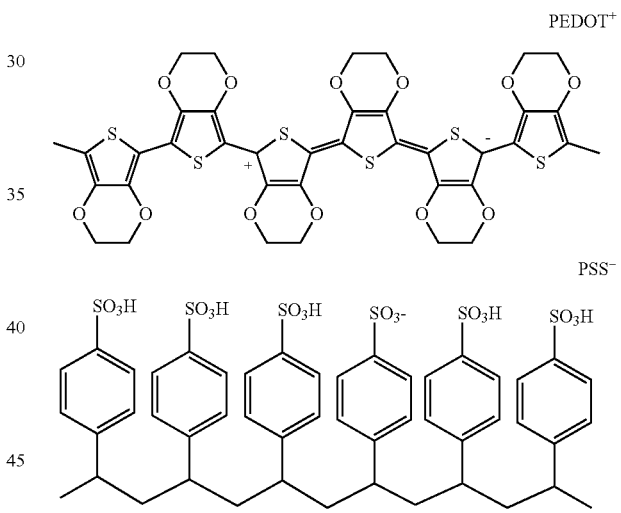

Figure 4:
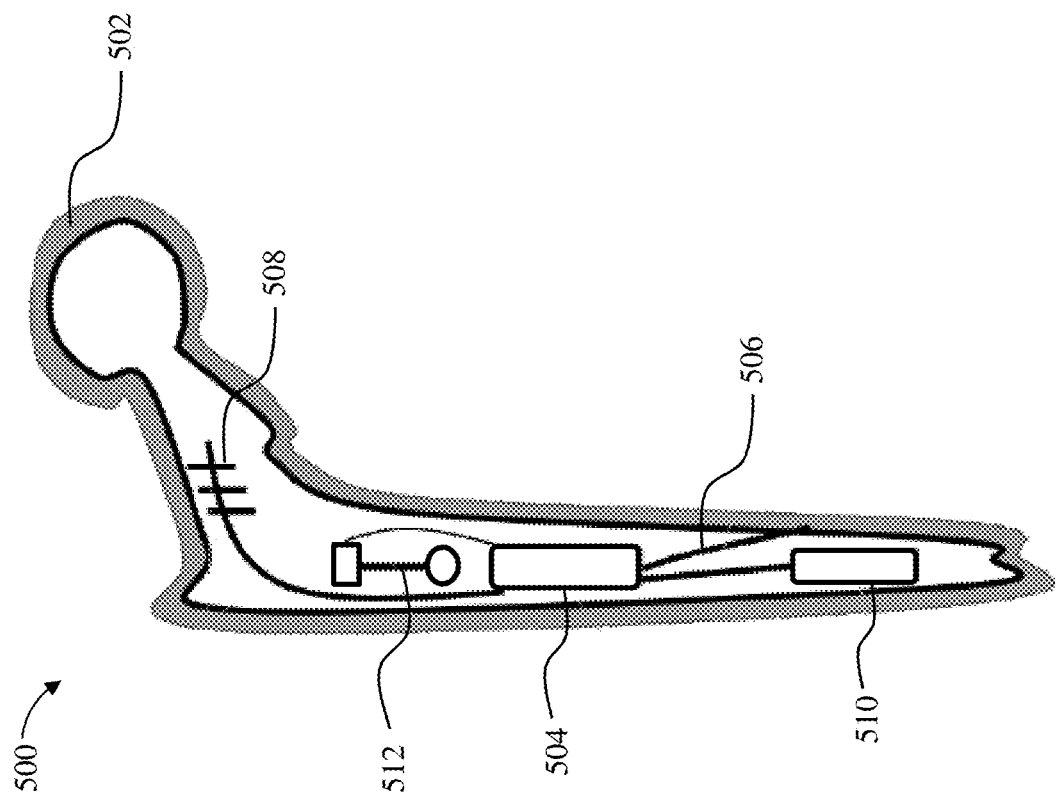
FIG. 4 depicts a prosthetic hip joint coated by a negatively charged coating during an intermediate operation of a method of fabricating an implantable medical device with a negatively charged surface according to one or more embodiments of the present invention.

In some embodiments, a surface of a device (i.e., an implantable medical device) is negatively charged using an electrode to prevent and treat bacterial and microorganism colonization, biofilm formation, and infection. FIG. 4 depicts a prosthetic hip joint 500 coated by a negatively charged coating 502 during an intermediate operation of a method of fabricating an implantable medical device with a negatively charged surface according to one or more embodiments. For ease of illustration only a single medical device (e.g., prosthetic hip joint 500) is depicted. It is understood that a variety of medical devices can be negatively charged using an electrode in a similar manner. In some embodiments, the medical device is a prosthetic heart valve, a left ventricular assist device, vascular stents, vascular grafts, a prosthetic joint, a bone implant, an implanted tooth, an implanted pacemaker, a pacemaker generator or wires, an intravascular line, a ventriculoperitoneal shunt, a urinary catheter, an eye implant, an intracranial implant, or a subcutaneous implant.

In some embodiments, the negative charge of the coating 502 is maintained by a power source 504. The power source 504 can be any suitable power source for implantable medical devices, such as, for example, a battery or a microcapacitor connected through an electrode 506 to the negatively charged coating 502. In some embodiments, the power source can be integrated with or functionally connected to the implantable device. In some embodiments, the power source can be charged from outside the patient body using induction, RFID or ultrasound through a wireless transmitter/receiver 508. In some embodiments, the wireless transmitter/receiver 508 is functionally connected with a control unit 510 including a digital computer. In some embodiments, the negatively charged coating 502 can be made of a nanowire mesh capable of generating electric energy (current) from mechanical movement. In this manner, movement of the negatively charged coating 502 charges the power source 504. In some embodiments, a mechanical energy transformer 512 embedded within the prosthetic hip joint 500 generates electric energy (current) from both body movements and the power source 504. In some embodiments, control unit 510 can wirelessly send and receive data from outside the patient's body.

In some embodiments, the negative charge of the coating 502 is triggered by the presence of indicators of potential infection, such as, for example, a change in local pH (indicating, e.g., a result of microbial metabolism) or a rise in body temperature (indicating, e.g., that a fever is present). In some embodiments, the negative charge of the coating 502 is maintained for a particular period, such as, for example, a period of time following implantation, a period of time following systemic infection, or a period of time as determined by a control signal received from a remote location (i.e., a control module located outside the body) through the wireless transmitter/receiver 508.

Materials, Preparation, and Characterization

Glyoxal (40 wt % in $H_2O$), aspartic acid, glycolic acid, 2-carboxyethyl acrylate and BPEI ($M_n$=10,000 g/mol) were sourced from Aldrich. (3-Aminopropyl)triethoxysilane (APTES) was sourced from Gelest. BPEI ($M_n$=1,800 g/mol) was sourced from Jeffamine. D4000 was sourced from Hunstman. MeO-PEG2 k-$NH_2$ was sourced from Polymer Science, Inc. All materials were used without further purification. $NH_2$-PEG4.6 k-$NH_2$ was prepared using known procedures. S. aureus (ATCC No. 6538) and P. aeruginosa (ATCC No. 9027) were sourced from ATCC. Mueller-Hinton Broth (MHB) was sourced from BD, Singapore. XTT salt (2,3-bis (2-methoxy-4-nitro-5-sulfo-phenyl)-2H-tetrazolium-5-carboxanilide) was sourced from Sigma Aldrich. LIVE/DEAD BacLight bacterial viability kit was sourced from Thermofisher.

Glass substrates were prepared by dipping 3" by 2" glass microscope slides in a surfactant solution overnight. The slides were then rinsed with water and ethanol and dried. The slides were then treated by UV/ozone for 15 minutes. Clean slides were dipped in a 10% APTES solution in ethanol for 30 minutes and thoroughly rinsed with ethanol before drying. Aluminum tape (e.g., 80 μm thickness) boundaries were installed and the slides were kept under nitrogen before spray coating.

Thermogravimetric analyses (TGA) was performed on a Q500. The samples (e.g., 5 to 7 mg) were scanned from room temperature to 500 degrees Celsius at a 5 degrees Celsius per min heating rate under an $N_2$ atmosphere. Differential scanning calorimetry (DSC) analyses were performed on a TA Instruments Q2000. The samples (e.g., 5 to 7 mg) were scanned from room temperature to 200 degrees Celsius at a 5 degrees Celsius per min heating rate in aluminum closed pans. Dynamic Mechanical Analyses (DMA) were performed on a TA Instruments DMA 2980 using a dual cantilever. The samples (approx. 12 by 6 by 1 mm deposited on metal screens) were solicited from −80 degrees Celsius to 200 degrees Celsius at a 5 degrees Celsius per min heating rate.

Procedure for the Preparation of PEI-Glyoxal Films by Spray-Coating

A 2.5 wt % glyoxal solution in water was transferred into the 22 mL-reservoir of a first spray gun. A second solution of 0.563 g $PEI_{1.8\ k}$ (0.31 mmol or 3.19 mmol —$NH_2$ moieties) in 6.8 g MilliQ water was transferred to the 22 mL-reservoir of a second spray gun. The layers were alternatively sprayed on a APTES-functionalized glass substrate (starting with the glyoxal solution) at a distance between the substrate and the nozzle of about 15 cm at a pressure of about 25 psi until the desired total number of layers was reached (e.g., a total of 9 layers). The glass substrate was then transferred on a hot plate for cure. The following thermal treatment was used: 30 degrees Celsius for 1 hour, 30 degrees Celsius to 120 degrees Celsius over 1 hour, and 120 degrees Celsius for 1 hour. After curing the film was allowed to cool down to room temperature. A piece of the film was scraped from the surface with a razor blade for thermal analysis. Alternatively, the same solutions were sprayed on a metal screen and analyzed by DMA.

Characterization of Antimicrobial/Antifouling Properties

Bacteria S. aureus and P. aeruginosa (0.5 mL, $10^5$ CFU/mL) in MHB medium were seeded on sample surfaces (0.5 cm by 0.5 cm) in a 48-well plate. After incubating for 24 hours the samples were washed with sterile PBS three times. The antimicrobial/antifouling properties were then assessed by XTT assay and live/dead bacteria staining. XTT salt (2,3-bis (2-methoxy-4-nitro-5-sulfo-phenyl)-2H-tetrazolium-5-carboxanilide) (50 μL 1 mg/mL) and menadione (10 μL, 0.4 mM) were incubated with PBS-washed samples at 37 degrees Celsius for 4 hours. The absorbance at 490 nm was recorded by a TECAN microplate reader. As viable bacterial cells convert XTT to orange color formazan, the absorption at 490 nm is correlated with metabolic activity of bacteria on surfaces. To visualize the bacteria on surfaces, a LIVE/DEAD Baclight bacterial viability kit was used to stain the bacteria. A dye solution of propidium iodide (staining bacteria with damaged membrane) and SYTO® 9 (staining bacteria with both intact membrane) was prepared by adding 1.5 μL of each dye stock into 1 mL PBS. The PBS-washed samples were stained by incubation with dye solution (500 μL) in dark for least 15 minutes. The fluorescence images were obtained using a Zesis LSM confocal microscope. Bacterial growth medium MHB was replaced daily with fresh MHB medium for the evaluation of long-term antimicrobial/antifouling properties. XTT assay and live/dead bacteria staining were conducted after incubation for 7 days, as described in detail above.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments described herein.

What is claimed is:

1. A method for forming a negatively charged polymer coating, the method comprising:
   providing a surface of an implantable medical device;
   providing a polymer comprising poly(3,4-ethylenedioxythiophene) (PEDOT); and
   functionalizing the polymer with a bio-compatible moiety comprising a negative Zeta potential and being polystyrene sulfonate group to form the negatively charged polymer coating on the surface of the implantable medical device.

2. The method of claim 1, wherein the implantable medical device is selected from the group consisting of a prosthetic heart valve, a left ventricular assist device, vascular stents, vascular grafts, a prosthetic joint, a bone implant, an implanted tooth, an implanted pacemaker, a pacemaker generator or wires, an intravascular line, a ventriculoperitoneal shunt, a urinary catheter, an eye implant, an intracranial implant, or a subcutaneous implant.

3. The method of claim 1, wherein the implantable medical device further comprises a power source.

4. The method of claim 3, wherein the power source is embedded within the implantable medical device.

5. The method of claim 4, wherein the power source comprises a battery.

6. The method of claim 4, wherein the power source comprises a microcapacitor coupled to the negatively charged coating through an electrode.

7. The method of claim 4, wherein the negatively charged coating is maintained by the power source.

8. The method of claim 4, wherein the power source is triggered to maintain the negatively charged coating by a change in local pH.

9. The method of claim 4, wherein the power source is triggered to maintain the negatively charged coating by a rise in body temperature.

10. The method of claim 4, wherein the power source is triggered to maintain the negatively charged coating for a period of time following implantation of the implantable medical device.

11. The method of claim 4, wherein the power source is triggered to maintain the negatively charged coating for a period of time determined by a control signal received from a remote location.

12. The method of claim 11, wherein the control signal is received from the remote location through a wireless transmitter.

13. The method of claim 12, wherein the wireless transmitter is embedded within the implantable medical device.

14. The method of claim 4, wherein the power source is charged using induction.

15. The method of claim 4, wherein the power source is charged through RFID or ultrasound through a wireless transmitter.

16. A method for forming a negatively charged coating, the method comprising:
   providing a surface of an implantable medical device;
   providing hydroxyapatite;
   functionalizing the hydroxyapatite with a bio-compatible moiety comprising a negative Zeta potential and being carboxylate groups to form the negatively charged coating on the surface of the implantable medical device.

17. The method of claim 16, wherein the carboxylate group is derived from dodecanedioic acid.

* * * * *